(12) United States Patent
Takahashi et al.

(10) Patent No.: US 12,263,039 B2
(45) Date of Patent: Apr. 1, 2025

(54) ULTRASONIC DIAGNOSTIC APPARATUS AND ULTRASONIC DIAGNOSTIC METHOD

(71) Applicant: Canon Medical Systems Corporation, Otawara (JP)

(72) Inventors: Hiroki Takahashi, Nasushiobara (JP); Gen Nagano, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 130 days.

(21) Appl. No.: 18/158,674

(22) Filed: Jan. 24, 2023

(65) Prior Publication Data

US 2023/0233188 A1 Jul. 27, 2023

(30) Foreign Application Priority Data

Jan. 26, 2022 (JP) .................................. 2022-010425

(51) Int. Cl.
*A61B 8/08* (2006.01)
*A61B 8/00* (2006.01)

(52) U.S. Cl.
CPC ................................. *A61B 8/5207* (2013.01)

(58) Field of Classification Search
CPC ........................... A61B 8/5223; A61B 8/5207
See application file for complete search history.

(56) References Cited

U.S. PATENT DOCUMENTS

2017/0071569 A1    3/2017  Sato
2017/0071575 A1*   3/2017  Sato ..................... A61B 8/5223

FOREIGN PATENT DOCUMENTS

JP    2017-55845 A    3/2017

\* cited by examiner

*Primary Examiner* — Gerald Johnson
(74) *Attorney, Agent, or Firm* — Oblon, McClelland, Maier & Neustadt, L.L.P.

(57) ABSTRACT

According to one embodiment, an ultrasonic diagnostic apparatus includes processing circuitry. The processing circuitry extracts an odd harmonic component from a reflected wave signal received by each element of an ultrasonic probe. The processing circuitry determines whether the reflected wave signal is saturated or not using the extracted odd harmonic component. The processing circuitry multiplies the reflected wave signal of an element for which the reflected wave signal is determined to be saturated by a weight coefficient. The processing circuitry generates reflected wave data by performing phasing addition on the reflected wave signal.

11 Claims, 6 Drawing Sheets

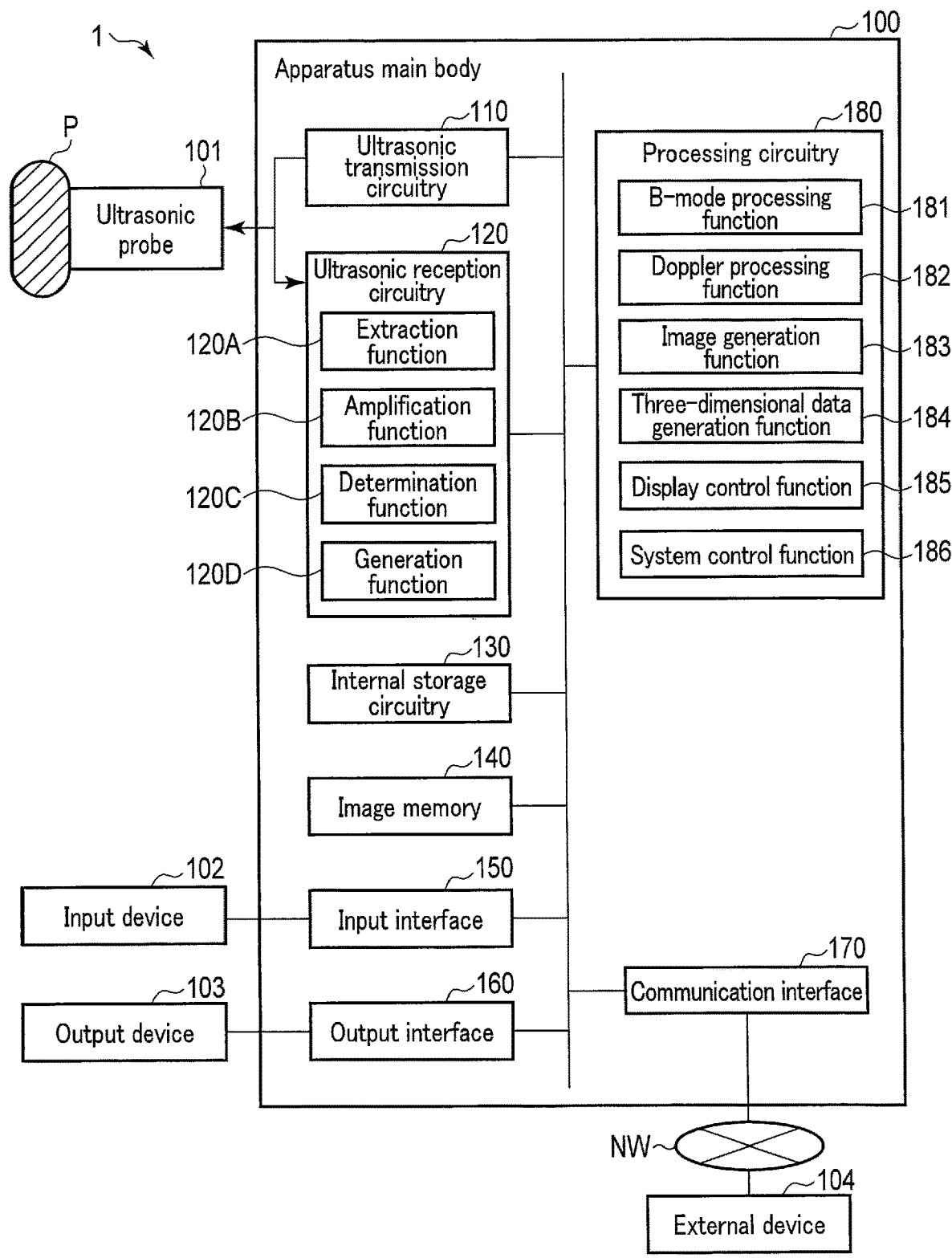
F I G. 1

ULTRASONIC DIAGNOSTIC APPARATUS AND ULTRASONIC DIAGNOSTIC METHOD

CROSS-REFERENCE TO RELATED APPLICATION(S)

This application is based upon and claims the benefit of priority from Japanese Patent Application No. 2022-010425, filed Jan. 26, 2022, the entire contents of which are incorporated herein by reference.

FIELD

Embodiments described herein relate generally to an ultrasonic diagnostic apparatus and an ultrasonic diagnostic method.

BACKGROUND

In a general ultrasonic diagnostic apparatus, analog circuitry performs various types of processing in order to create an image of reflected wave signals (echo signals) of ultrasonic waves from a living body. There is a case where the analog circuitry amplifies to a large degree weak reflected wave signals from a deep part of a living body or the like in order to create an image of the signals (e.g., harmonic imaging, imaging of a bloodstream having a small scattering coefficient). In this case, the amplified signals exceed the dynamic range of the analog circuitry, and signal saturation occurs. When signal saturation occurs, the phase of a received echo is modulated; thus, its influence is observed, for example, in the form of an increase in a side lobe artifact in the image or an appearance of a non-linear component (high-brightness point). Therefore, for the purpose of improving the visibility of an image, it is required to reduce the influence of signal saturation on imaging while fully maintaining biological information.

In order to achieve the above object, there is a method in which, for example, after determining whether reflected wave signals received by each element of an ultrasonic probe are saturated or not based on a threshold, a contribution of the reflected wave signals that are determined to be saturated is decreased to create an image. In this method, however, there is a fear of erroneously determining signals that are actually not saturated (i.e., unsaturated signals) to be signals that are saturated (i.e., saturated signals) and decreasing a contribution of the unsaturated signals. This causes reduction of the number of elements contributing to imaging (effective aperture), making it impossible to fully achieve the above-described object.

BRIEF DESCRIPTION OF THE DRAWING(S)

FIG. 1 is a diagram showing an example of a configuration of an ultrasonic diagnostic apparatus according to a first embodiment.

DETAILED DESCRIPTION

Figure 2:
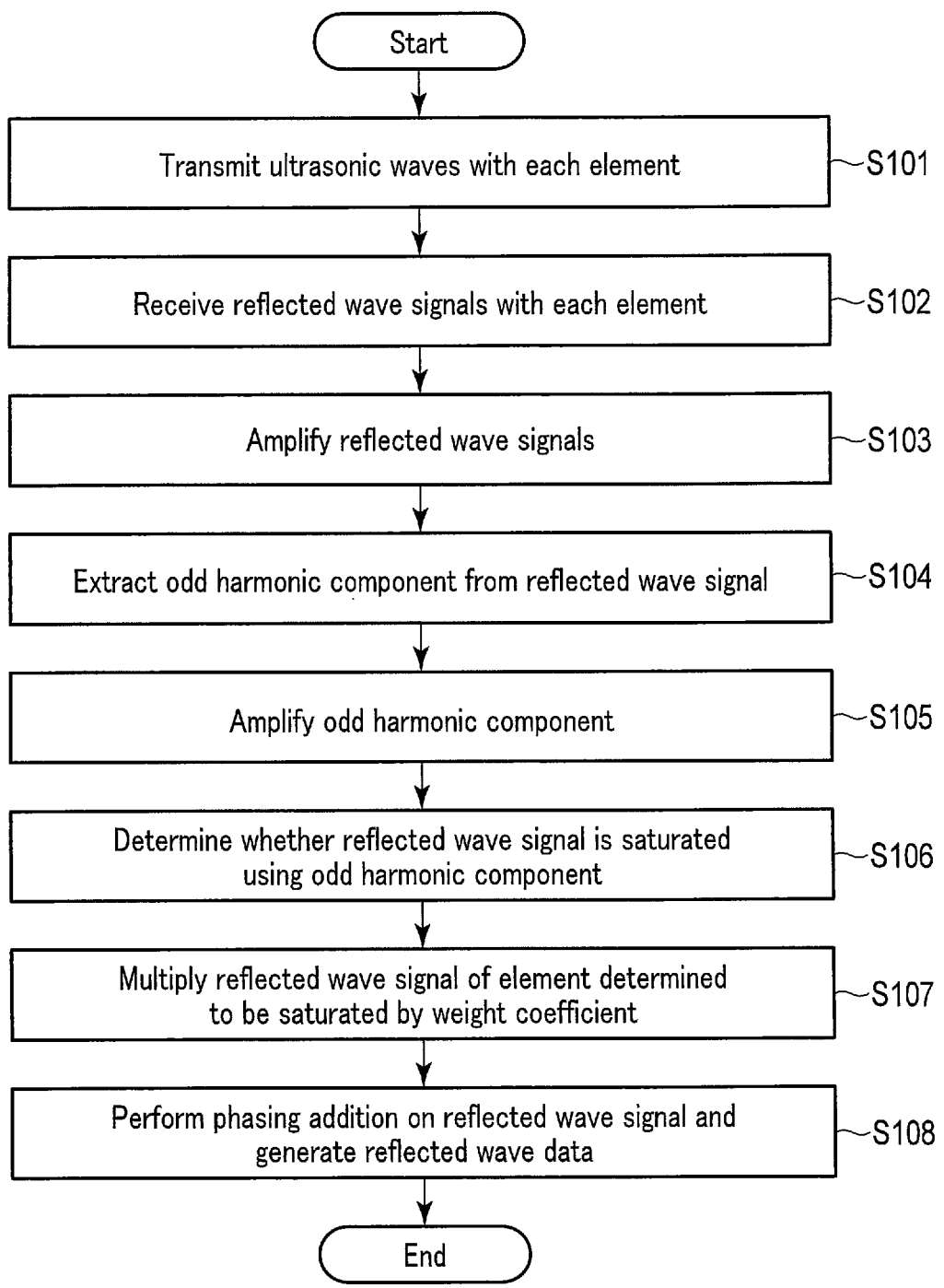
FIG. 2 is a diagram showing an example of an operation of the ultrasonic diagnostic apparatus according to the first embodiment.

In general, according to one embodiment, an ultrasonic diagnostic apparatus includes processing circuitry.

The processing circuitry extracts an odd harmonic component from a reflected wave signal received by each element of an ultrasonic probe. The processing circuitry determines whether the reflected wave signal is saturated or not using the extracted odd harmonic component. The processing circuitry multiplies the reflected wave signal of an element for which the reflected wave signal is determined to be saturated by a weight coefficient. The processing circuitry generates reflected wave data by performing phasing addition on the reflected wave signal.

Hereinafter, an ultrasonic diagnostic apparatus and an ultrasonic diagnostic method according to embodiments will be described with reference to the drawings. In the embodiments described below, elements assigned the same reference numerals perform the same operations, and redundant descriptions will be omitted, as appropriate.

First Embodiment

FIG. 1 is a diagram showing an example of a configuration of an ultrasonic diagnostic apparatus 1 according to a first embodiment. The ultrasonic diagnostic apparatus 1 includes an apparatus main body 100 and an ultrasonic probe 101. The apparatus main body 100 is connected to an input device 102 and an output device 103. The apparatus main body 100 is connected to an external device 104 via a network NW. The external device 104 is, for example, a server equipped with a picture archiving and communication system (PACS).

The ultrasonic probe 101 executes ultrasound scanning in a scan area of a living body P, which is a subject, under the control of the apparatus main body 100. The ultrasonic probe 101 includes, for example, a plurality of piezoelectric vibrators (also referred to as "elements"), a matching layer provided between a case and the plurality of piezoelectric vibrators, and a backing material that prevents ultrasonic waves from propagating backward with respect to a transmission direction of the ultrasonic waves from the plurality of piezoelectric vibrators. The ultrasonic probe 101 is a two-dimensional array probe in which a plurality of piezoelectric vibrators are aligned along, for example, a first element alignment direction (elevation direction) and a second element alignment direction (azimuth direction). The ultrasonic probe 101 is detachably connected to the apparatus main body 100. The ultrasonic probe 101 may be provided with buttons which are pressed when offset processing, an operation for freezing an ultrasonic image (freeze operation), and the like are performed.

The piezoelectric vibrators generate ultrasonic waves based on a drive signal supplied from ultrasonic transmission circuitry 110 of the apparatus main body 100. Thus, ultrasonic waves are transmitted from the ultrasonic probe 101 to the living body P. The transmitted ultrasonic waves are sequentially reflected on the acoustic impedance discontinuous surfaces of the body tissue of the living body P, and are received as reflected wave signals by the piezoelectric vibrators. The amplitude of the received reflected wave signals depends on the difference in the acoustic impedance on the discontinuous surface. If the transmitted ultrasonic waves are reflected from the surface of a moving object (such as red blood cells, a cardiac wall, or a contrast agent), the frequency of the resultant reflected wave signals are shifted due to the Doppler effect, with the shift depending on the velocity component in the ultrasonic transmission direction of the moving object. The ultrasonic probe 101 receives the reflected wave signals from the living body P, and converts them into electric signals.

In this embodiment, a single ultrasonic probe 101 is connected to the apparatus main body 100. In another embodiment, a plurality of ultrasonic probes 101 are connected to the apparatus main body 100. Which of the connected ultrasonic probes 101 is to be used for the ultrasound scanning can be determined discretionarily by using a software button on a touch panel.

The apparatus main body 100 is a device that generates an ultrasonic image based on the reflected wave signals received by the ultrasonic probe 101. The apparatus main body 100 includes ultrasonic transmission circuitry 110, ultrasonic reception circuitry 120, internal storage circuitry 130, an image memory 140, an input interface 150, an output interface 160, a communication interface 170, and processing circuitry 180.

The ultrasonic transmission circuitry 110 is a processor that supplies a drive signal to the ultrasonic probe 101. The ultrasonic transmission circuitry 110 is constituted by, for example, trigger generation circuitry, delay circuitry, and pulser circuitry. The trigger generation circuitry repeatedly generates rate pulses for forming transmission ultrasonic waves at a predetermined rate frequency. The delay circuitry gives the generated rate pulses a delay time for each piezoelectric vibrator. By varying a delay time for each piezoelectric vibrator, the transmission directions of the ultrasonic waves from the piezoelectric vibrators are discretionarily adjusted. That is, the delay circuitry determines the transmission directivity of the ultrasonic waves generated from the ultrasonic probe 101. The pulser circuitry applies a drive signal (drive pulse) to the piezoelectric vibrators of the ultrasonic probe 101 at a timing based on the rate pulse.

The ultrasonic transmission circuitry 110 discretionarily changes the output intensity of the transmission ultrasonic waves through the drive signal. For example, the ultrasonic diagnostic apparatus 1 reduces the influence of the attenuation of the ultrasonic waves inside the living body P by increasing the output intensity. Thus, the ultrasonic diagnostic apparatus 1 can obtain a reflected wave signal having a large S/N (signal/noise) ratio when receiving the signal.

When the ultrasonic waves are propagated inside the living body P, the strength of the oscillation of the ultrasonic waves corresponding to the output intensity (the strength is also referred to as "acoustic power") is attenuated. The attenuation of the acoustic power is caused by absorption, scattering, reflection, and the like. The degree of attenuation of the acoustic power depends on the frequency and the propagation distance of the ultrasonic waves. For example, the degree of attenuation is increased by increasing the frequency of the ultrasonic waves. Also, the longer the propagation distance of the ultrasonic waves, the larger the degree of attenuation.

The ultrasonic reception circuitry 120 is a processor that performs various types of processing on the reflected wave signals received by the ultrasonic probe 101 and generates reflected wave data. Specifically, the ultrasonic reception circuitry 120 is implemented by, for example, amplifier circuitry, A/D (analog-digital) converter circuitry, quadrature detection (IQ) circuitry, and generator circuitry (also referred to as a "beamformer"). The amplifier circuitry performs gain correction processing by amplifying the reflected wave signals received by the ultrasonic probe 101 for each element. The A/D converter circuitry converts the reflected wave signals after the gain correction into digital signals. The quadrature detection circuitry converts the digital signals into in-phase signals (I-signals, I: in-phase) and quadrature-phase signals (Q-signals, Q: quadrature-phase) in a baseband bandwidth. The I-signals and Q-signals are examples of baseband signals. The generator circuitry gives the baseband signals a delay time needed to determine the reception directivity and performs phasing addition on the baseband signals (i.e., I-signals and Q-signals) given the delay time. Through the phasing addition performed by the generator circuitry, reflected wave data with enhanced signal components from a direction corresponding to the reception directivity is generated. The generated reflected wave data is transferred to the processing circuitry 180.

The ultrasonic reception circuitry 120 is an example of analog circuitry. The ultrasonic reception circuitry 120 may be installed in each of the elements, or a single ultrasonic reception circuitry 120 may be installed for the whole set of elements.

In this embodiment, the ultrasonic reception circuitry 120 includes at least one processor. The term "processor" means circuitry such as a CPU (central processing unit), a GPU (graphics processing unit), an ASIC (application specific integrated circuit), a programmable logic device (for example, an SPLD (simple programmable logic device), a CPLD (complex programmable logic device), or an FPGA (field programmable gate array)), etc. If the processor is a CPU, the processor implements each function by reading and executing the program stored in the internal storage circuitry 130. On the other hand, if the processor is an ASIC, each function is directly incorporated into the circuitry of the processor as a logic circuit, instead of a program being stored in the internal storage circuitry 130. The processor may be constituted as single circuitry or a combination of independent sets of circuitries. The ultrasonic reception circuitry 120 implements each function (e.g., an extraction function 120A, an amplification function 120B, a determination function 120C, and a generation function 120D).

The extraction function 120A extracts an odd harmonic component from the reflected wave signal received by each of the elements of the ultrasonic probe 101. For example, the extraction function 120A extracts an odd harmonic component from the reflected wave signal by applying frequency filtering processing for passing through an odd harmonic band on the reflected wave signal received by each of the elements of the ultrasonic probe 101. The extraction function 120A may be implemented by filter circuitry.

The amplification function 120B amplifies the amplitude of the extracted odd harmonic component with a gain value. The gain value may be a predetermined value. The amplification function 120B may also determine a gain value according to the amplitude of the extracted odd harmonic component and amplify the amplitude with the determined gain value. The amplification function 120B may be implemented by amplifier circuitry.

The determination function 120C determines whether the reflected wave signal is saturated or not using the extracted odd harmonic component. For example, the determination function 120C determines that the reflected wave signal is saturated if the amplitude of the extracted odd harmonic component is equal to or greater than a threshold. In particular, if the extracted odd harmonic component is amplified, the determination function 120C determines that the reflected wave signal is saturated when the amplitude of the amplified odd harmonic component is equal to or greater than a threshold. The determination function 120C may be implemented by comparison circuitry.

The generation function 120D multiplies the reflected wave signal of the element determined to be saturated by a weight coefficient. Also, the generation function 120D generates reflected wave data by performing phasing addition on the reflected wave signal multiplied by a weight coefficient. The generation function 120D may be implemented by the generator circuitry of the ultrasonic reception circuitry 120.

The internal storage circuitry 130 includes a processor-readable storage medium (e.g., a magnetic storage medium, an optical storage medium, a semiconductor memory). The internal storage circuitry 130 stores various types of data including programs related to ultrasonic transmission and reception and image generation processing. The various types of data may be stored in advance in the internal storage circuitry 130. The various types of data may also be stored in a non-transitory storage medium to be distributed, and read from the non-transitory storage medium to be installed in the internal storage circuitry 130. The internal storage circuitry 130 stores various types of data (e.g., B-mode image data, contrast image data, image data related to a bloodstream image, three-dimensional data) that are generated by the processing circuitry 180, in accordance with an operation input via the input interface 150. The internal storage circuitry 130 may transfer the various types of data to the external device 104 via the communication interface 170.

The internal storage circuitry 130 may be a drive which reads and writes various types of information to and from a portable storage medium (e.g., a CD drive, a DVD drive, a flash memory). The internal storage circuitry 130 may write the stored data into a portable storage medium and store the data in the external device 104 through the portable storage medium.

The image memory 140 includes a processor-readable storage medium (e.g., a magnetic storage medium, an optical storage medium, a semiconductor memory). For example, the image memory 140 stores image data corresponding to a plurality of frames immediately before a freeze operation input via the input interface 150. The image data stored in the image memory 140 may be continuously displayed (cine-displayed). The image memory 140 may store not only image data but also three-dimensional data.

The internal storage circuitry 130 and the image memory 140 need not necessarily be realized by independent storage devices. The internal storage circuitry 130 and the image memory 140 may be realized by a single storage device. Each of the internal storage circuitry 130 and the image memory 140 may be realized by a plurality of storage devices.

The input interface 150 receives various commands from an operator through the input device 102. Examples of the input device 102 include a mouse, a keyboard, a panel switch, a slider switch, a trackball, a rotary encoder, an operation panel, and a touch panel. The input interface 150 is connected to the processing circuitry 180 via a bus, for example, so that it converts, into an electric signal, an operation command input by an operator and outputs the electric signal to the processing circuitry 180. The input interface 150 is not limited to one that is connected to physical operation components such as a mouse and a keyboard. Examples of the input interface 150 include circuitry which receives an electric signal corresponding to an operation command input from an external input device provided separately from the ultrasonic diagnostic apparatus 1 and outputs the received electric signal to the processing circuitry 180. The operators are, for example, a doctor, a nurse, an assistant nurse, a clinical radiologist, and a clinical laboratory technician.

The output interface 160 is an interface for outputting, for example, an electric signal from the processing circuitry 180 to the output device 103. The output device 103 is any display such as a liquid crystal display, an organic EL display, an LED display, a plasma display, or a CRT display. The output device 103 may be a touch-panel display that also serves as the input device 102. The output device 103 is not only a display but may also be a speaker that outputs voice. The output interface 160 is connected to the processing circuitry 180, for example, via a bus, and outputs the electric signal from the processing circuitry 180 to the output device 103.

The communication interface 170 is connected to the external device 104 via, for example, the network NW, and performs data communication with the external device 104.

The processing circuitry 180 controls the entire operation of the ultrasonic diagnostic apparatus 1. In this embodiment, the processing circuitry 180 includes at least one processor. As described above, the term "processor" means circuitry such as a CPU, a GPU, an application specific integrated circuit, etc. Specifically, the processing circuitry 180 implements each function (e.g., a B-mode processing function 181, a Doppler processing function 182, an image generation function 183, a three-dimensional data generation function 184, a display control function 185, a system control function 186).

The B-mode processing function 181 is a function of generating B-mode data based on the reflected wave data transferred from the ultrasonic reception circuitry 120. Specifically, with the B-mode processing function 181, the processing circuitry 180 performs envelope detection processing, logarithmic compression processing, etc., on the reflected wave data and generates B-mode data that expresses a signal intensity of the reflected wave data by a brightness value. The generated B-mode data is stored in a RAW data memory (not shown) as B-mode RAW data on two-dimensional ultrasound scan lines (rasters).

Also, the processing circuitry 180 can perform harmonic imaging with the B-mode processing function 181. The harmonic imaging uses a harmonic component among various frequency components included in the reflected wave signals of ultrasound. The harmonic imaging is classified into tissue harmonic imaging (THI) that does not use a contrast agent and contrast harmonic imaging (CHI) that uses a contrast agent.

In the THI, a harmonic component is extracted using an amplitude modulation (AM) method, a phase modulation (PM) method, or an imaging method referred to as an AMPM method, which is a combination of the AM method and the PM method.

In the AM method, the PM method, and the AMPM method, ultrasonic transmission is performed more than once for the same scanning line, with different amplitudes and/or phases. Through the above process, the ultrasonic reception circuitry 120 generates multiple pieces of reflected wave data at each scanning line and outputs the generated reflected wave data. With the B-mode processing function 181, the processing circuitry 180 performs addition-subtraction processing on the multiple pieces of reflected wave data at each scanning line in accordance with a modulation method, and thereby extracts a harmonic component. Also, the processing circuitry 180 performs envelope detection processing, etc., on the reflected wave data of the harmonic component to generate B-mode data.

In the CHI, a harmonic component is extracted using, for example, a frequency filter. With the B-mode processing function 181, the processing circuitry 180 separates reflected wave data (a fundamental wave component) whose reflection source is a tissue in the living body P from reflected wave data (a harmonic component) whose reflection source is a contrast agent. Thus, the processing circuitry 180 can select a harmonic component from the contrast agent using a frequency filter and generate B-mode data to generate contrast image data.

For example, with the B-mode processing function 181 (an example of a controller), the ultrasonic diagnostic apparatus 1 may cause the ultrasonic probe 101 to perform ultrasound scanning with a set of a first transmission ultrasonic wave and a second transmission ultrasonic wave having a phase corresponding to the inverted phase of the first transmission ultrasonic wave. Subsequently, with the extraction function 120A, the ultrasonic diagnostic apparatus 1 may add the reflected wave signal of the first transmission ultrasonic wave and the reflected wave signal of the second transmission ultrasonic wave that are received by each element of the ultrasonic probe 101 and extract an odd harmonic component from the added reflected wave signals by applying frequency filtering processing for passing through an odd harmonic band to the added reflected wave signals. Thus, the ultrasonic diagnostic apparatus 1 can extract an odd harmonic component from reflected wave signals.

Also, with the B-mode processing function 181 (an example of a controller), the ultrasonic diagnostic apparatus 1 may cause the ultrasonic probe 101 to perform ultrasound scanning with a set of a first transmission ultrasonic wave, a second transmission ultrasonic wave having a phase corresponding to the phase of the first transmission ultrasonic wave modulated at N degrees (N being a real number satisfying 0<N<180) in the positive direction, and a third transmission ultrasonic wave having a phase corresponding to the phase of the first transmission ultrasonic wave modulated at N degrees in the negative direction. Subsequently, with the extraction function 120A, the ultrasonic diagnostic apparatus 1 adds the reflected wave signal of the first transmission ultrasonic wave, the reflected wave signal of the second transmission ultrasonic wave, and the reflected wave signal of the third transmission ultrasonic wave that are received by each element of the ultrasonic probe 101 and extracts an odd harmonic component from the added reflected wave signals by applying frequency filtering processing for passing through an odd harmonic band to the added reflected wave signals. Thus, the ultrasonic diagnostic apparatus 1 can extract an odd harmonic component from reflected wave signals.

The B-mode data used to generate contrast image data is data representing, as a brightness value, the echo reflection intensity of the wave whose reflection source is a contrast agent. The processing circuitry 180 can also extract a fundamental wave component from the reflected wave data of the living body P and generate B-mode data for generating living tissue image data.

The Doppler processing function 182 is a function to generate data (Doppler information) as an extraction of Doppler effect-based motion information of a moving object that is present within a region of interest (ROI) set in a scan region, and this data is generated through a frequency analysis of the reflected wave data transferred from the ultrasonic reception circuitry 120. The generated Doppler information is stored in a RAW data memory (not shown) as Doppler RAW data (also referred to as "Doppler data") on the two-dimensional ultrasonic scanning lines.

Specifically, with the Doppler processing function 182, the processing circuitry 180 estimates an average velocity, an average dispersion value, an average power value, etc., for example, as motion information of a moving object at each sampling point, and generates Doppler data indicating the estimated motion information. With the Doppler processing function 182, the processing circuitry 180 estimates an average bloodstream velocity, a dispersion value of a bloodstream velocity, a power value of a bloodstream signal, etc., as motion information of a bloodstream (bloodstream information) at each sampling point, and generates Doppler data indicating the estimated bloodstream information.

The image generation function 183 is a function of generating B-mode image data based on the B-mode data generated by the B-mode processing function 181. With the image generation function 183, the processing circuitry 180, for example, converts (scan-converts) a scanning line signal sequence of an ultrasonic scan into a scanning line signal sequence of a video format representatively used by television, etc. to generate image data for display (display image data). Specifically, the processing circuitry 180 executes RAW-pixel conversion, such as coordinate conversion corresponding to the mode of the ultrasonic scan by the ultrasonic probe 101, on B-mode RAW data stored in the RAW data memory to generate two-dimensional B-mode image data (also referred to as "ultrasonic image data") consisting of pixels. In other words, with the image generation function 183, the processing circuitry 180 generates a plurality of ultrasonic images (medical images) respectively corresponding to a plurality of consecutive frames through transmission and reception of ultrasonic waves.

The processing circuitry 180, for example, generates Doppler image data in which bloodstream information is visualized by performing RAW-pixel conversion on the Doppler RAW data stored in the RAW data memory. The Doppler image data is average velocity image data, distribution image data, power image data, or image data including any combination thereof. The processing circuitry 180 generates, as Doppler image data, color Doppler image data that represents the bloodstream information by color and Doppler image data that represents a piece of bloodstream information in a waveform shape in gray scale.

The three-dimensional data generation function 184 is a function of generating three-dimensional B-mode data (three-dimensional data) based on the reflected wave data received from the ultrasonic reception circuitry 120. In the three-dimensional data generation function 184, the processing circuitry 180 allocates a brightness value to a voxel located in a three-dimensional space using the B-mode data generated by the B-mode processing function 181, thereby generating three-dimensional data. The three-dimensional data may be referred to as volume data. Since the brightness value corresponds to the echo reflection intensity, it can be construed that the echo reflection intensity is allocated to the voxel of volume data.

The display control function 185 is a function of causing a display as the output device 103 to display an image based on various kinds of ultrasonic image data generated by the image generation function 183. With the display control function 185, the processing circuitry 180, for example, controls the displaying, on the display, of an image based on the B-mode image data, the Doppler image data, or the image data including both of these types of data, generated by the image generation function 183.

More specifically, with the display control function 185, the processing circuitry 180 converts (scan-converts) a scanning line signal sequence of an ultrasonic scan into a scanning line signal sequence of a video format representatively used by television, etc., to generate display image data. The processing circuitry 180 may also perform various types of processing, such as dynamic range, brightness, contrast, y curve corrections, and an RGB conversion, on the display image data. The processing circuitry 180 may add supplementary information, such as textual information of various parameters, a scale, or a body mark, to the display image data. The processing circuitry 180 may also generate a user interface (GUI: graphical user interface) for an operator to input various instructions through the input device, and cause a display to display the GUI.

The system control function 186 is a function to control the entire operation of the ultrasonic diagnostic apparatus 1 comprehensively. For example, with the system control function 186, the processing circuitry 180 controls the ultrasonic transmission circuitry 110 and the ultrasonic reception circuitry 120 based on a parameter related to transmission and reception of ultrasonic waves.

FIG. 2 is a diagram showing an example of an operation of the ultrasonic diagnostic apparatus 1 according to the first embodiment. In the example of the operation, each of transmission of an ultrasonic wave and reception of an ultrasonic wave is performed once. That is, processing of generating reflected wave data in the single transmission and reception of an ultrasonic wave is described. The example of the operation corresponds to a scan method (all-raster parallel simultaneous reception) in which a single plane-wave transmission or a wide-range transmission similar to a plane-wave transmission is performed to obtain an all-reception raster in an ultrasonic scan range in real time in a single transmission.

In step S101, the ultrasonic diagnostic apparatus 1 transmits ultrasonic waves with each element. Specifically, the ultrasonic diagnostic apparatus 1 generates ultrasonic waves based on a drive signal supplied from the ultrasonic transmission circuitry 110 in each element of the ultrasonic probe 101. Subsequently, the ultrasonic diagnostic apparatus 1 transmits the generated ultrasonic waves to a living body. The transmitted ultrasonic waves are sequentially reflected on the acoustic impedance discontinuous surfaces of the body tissue of the living body, as described above, whereby reflected waves are sequentially generated. The generated reflected waves propagate through the living body and reach each element of the ultrasonic probe 101.

In step S102, the ultrasonic diagnostic apparatus 1 receives reflected wave signals with each element. Specifically, the ultrasonic diagnostic apparatus 1 receives reflected wave signals by subjecting the reflected waves from the living body to piezoelectric conversion in each element of the ultrasonic probe 101. Thereby, reflected wave signals for each depth of the living body (or time) are received at each element. The reflected wave signals received are transferred from each element of the ultrasonic probe 101 to the ultrasonic reception circuitry 120 of the apparatus main body 100. Since the ultrasonic waves are attenuated to a greater degree as the propagation distance becomes longer, as described above, the reflected wave signals from the deep part of the living body are weaker. Therefore, in a specific application (e.g., harmonic imaging, imaging of a bloodstream having a small scattering coefficient), reflected wave signals need to be amplified greatly to carry out imaging.

In step S103, the ultrasonic diagnostic apparatus 1 amplifies the reflected wave signals. Specifically, the ultrasonic reception circuitry 120 of the ultrasonic diagnostic apparatus 1 performs gain correction processing by amplifying, for each depth, the reflected wave signals received from the respective elements. According to an example, the ultrasonic reception circuitry 120 amplifies the reflected wave signals by 18 dB and then passes the signals through 0 to −24 dB variable attenuation circuitry. This allows for imaging of weak reflected wave signals from the deep part of the living body. If the ultrasonic reception circuitry 120 need not amplify the reflected wave signals, this step may be omitted.

However, the dynamic range of the ultrasonic reception circuitry 120 has a limitation (of usually about 60 dB). Thus, reflected wave signals from, for example, a strong reflector (e.g., blood vessel wall, diaphragm) are saturated mainly in the amplifier circuitry of the ultrasonic reception circuitry 120. Namely, even when reflected wave signals are received by the same element, reflected wave signals from the depth where a strong reflector is present are saturated, whereas reflected wave signals from the depth where a strong reflector is not present may not be saturated. Also, in the color Doppler mode, reflected wave signals are received at a high gain value in order to obtain a weak bloodstream signal at a better S/N ratio. In this manner, if the reflected wave signals exceed the dynamic range of the ultrasonic reception circuitry 120, the reflected wave signals are saturated at the ultrasonic reception circuitry 120 and signal saturation occurs.

In this instance, the saturated reflected wave signals (saturated signals) include odd harmonic components augmented by saturation in addition to second- or higher-order harmonic components generated by a phenomenon in which a waveform is distorted as the ultrasonic waves propagate through the living body (this phenomenon is also referred to as "a non-linear effect"). For the sake of performance, circuitry protection, etc., the amplifier circuitry is designed so that if a signal having an intensity beyond the limitation of its amplification properties passes through it, the signal is clipped. A received signal s and a clipped received signal $s_{clip}$ are represented by the following formula:

$$s(t) = a \sin(\omega t)$$

$$S_{clip}(t) = \begin{cases} s(t), & |s(t)| < A_{th} \\ A_{th} \operatorname{sign}(s(t)), & |s(t)| \geq A_{th} \end{cases}$$

where a denotes an amplitude coefficient, ω denotes a reception angle frequency, $A_{th}$ denotes a threshold for clipping, and sign( ) denotes a function for returning a symbol. If the amplitude of the received signal is very large, that is, when a>>$A_{th}$ and |s(t)|≥$A_{th}$ in all time zones, a clipped received signal is represented by the following formula:

$$S_{clip}(t) = A_{th} \operatorname{sign}(s(t))$$
$$= \begin{cases} -A_{th}, & (2n-1)\pi < \omega t < (2n)\pi \\ A_{th}, & (2n)\pi < \omega t < (2n+1)\pi \end{cases}$$

This indicates that a clipped signal approaches a rectangular wave according to the degree of saturation of the signal, and the rectangular wave is known to have a frequency component that is an odd multiple of its period.

Thus, it is understood that the frequency characteristics of a saturated signal have not only a reception frequency but also a frequency component of an odd multiple thereof due to clipping. On the other hand, an unsaturated reflected wave signal (unsaturated signal) includes mainly a two- or higher-order harmonic component generated by this phenomenon. Therefore, whether a reflected wave signal is saturated or not can be discriminated with high precision based on an odd harmonic component included in the reflected wave signal. Thus, the ultrasonic diagnostic apparatus 1 extracts an odd harmonic component from a reflected wave signal.

In step S104, by implementing the extraction function 120A, the ultrasonic diagnostic apparatus 1 extracts an odd harmonic component from a reflected wave signal. Specifically, the ultrasonic reception circuitry 120 of the ultrasonic diagnostic apparatus 1 extracts an odd harmonic component from the reflected wave signal by applying frequency filtering processing for passing through an odd harmonic band to the reflected wave signal. The frequency filtering processing may be implemented by filter circuitry that allows a specific frequency component to pass therethrough. For example, if a frequency component to be extracted is a three-order harmonic component, filter circuitry (a high-pass filter) that allows a three- or higher-order frequency component to pass therethrough may be used. The ultrasonic reception circuitry 120 extracts a three-order odd harmonic component by making a reflected wave signal pass through the filter circuitry. A five- or higher-order odd harmonic component may be extracted in the same manner. As a matter of course, multiple types of odd harmonic components may be extracted. Also, an odd harmonic component may be extracted by performing arithmetic processing on received signals whose phases or amplitudes are modulated and which are obtained through multiple times of transmission, as in the case of the AM method and PM method adopted in harmonic imaging. The extraction of an odd harmonic component may be performed on reflected wave signals before and after A/D conversion is performed (i.e., an analog signal or a digital signal).

In step S105, by implementing the amplification function 120B, the ultrasonic diagnostic apparatus 1 amplifies an odd harmonic component. Specifically, the ultrasonic reception circuitry 120 of the ultrasonic diagnostic apparatus 1 amplifies the amplitude of the extracted odd harmonic component with a gain value. For example, the ultrasonic reception circuitry 120 determines a gain value according to the amplitude of the extracted odd harmonic component and amplifies the amplitude with the determined gain value. The gain value may be set to any value by an operator of the ultrasonic diagnostic apparatus 1 or incorporated in the form of hardware into the circuitry design of the ultrasonic reception circuitry 120. Performing amplification increases an amplitude difference between an amplitude of an odd harmonic component of a saturated reflected wave signal and an amplitude of a harmonic component of an unsaturated reflected wave signal. The ultrasonic diagnostic apparatus 1 can discriminate between a saturated signal and an unsaturated signal with more precision by setting a threshold to, for example, a middle value of the amplitude difference in threshold processing. In this manner, the ultrasonic diagnostic apparatus 1 can specifically detect a saturated signal. If the ultrasonic reception circuitry 120 need not amplify the odd harmonic component, this step may be omitted.

In step S106, by implementing the determination function 120C, the ultrasonic diagnostic apparatus 1 determines whether the reflected wave signal is saturated or not using the extracted odd harmonic component. Specifically, the ultrasonic reception circuitry 120 of the ultrasonic diagnostic apparatus 1 determines that the reflected wave signal is saturated if the amplitude of the extracted odd harmonic component is equal to or greater than a threshold. The threshold may be set to any value by an operator of the ultrasonic diagnostic apparatus 1 or incorporated in the form of hardware into the circuitry design of the ultrasonic reception circuitry 120. If multiple types of odd harmonic components are extracted, the ultrasonic reception circuitry 120 may determine the presence or absence of saturation based on the threshold set for each type of odd harmonic component.

In step S107, by implementing the generation function 120D, the ultrasonic diagnostic apparatus 1 multiplies the reflected wave signal of the element determined to be saturated by a weight coefficient. Specifically, the ultrasonic reception circuitry 120 of the ultrasonic diagnostic apparatus 1 multiplies the reflected wave signal of the element determined to be saturated by a weight coefficient in a range of 0 to 1, and thereby reduces the contribution of the reflected wave signal. As a matter of course, the ultrasonic reception circuitry 120 may set the value of the reflected wave signal determined to be saturated to 0. Thereby, the ultrasonic reception circuitry 120 can reduce the probability of the reflected wave signal from each element subjected to phasing addition being saturated.

In step S108, by implementing the generation function 120D, the ultrasonic diagnostic apparatus 1 generates reflected wave data by performing phasing addition on the reflected wave signal multiplied by a weight coefficient. As described above, the generated reflected wave data is transferred to the processing circuitry 180.

After performing phasing addition, the processing circuitry 180 implements the B-mode processing function 181 to generate B-mode data from the transferred reflected wave data. Subsequently, by implementing the image generation function 183, the processing circuitry 180 generates B-mode image data from the B-mode data. Thereafter, by implementing the display control function 185, the processing circuitry 180 causes the output device 103 as a display to display an ultrasonic image based on the B-mode image data. The displayed ultrasonic image is, for example, observed by the operator of the ultrasonic diagnostic apparatus 1 and used for medical diagnosis and the like.

The above is the description of the ultrasonic diagnostic apparatus 1 according to the first embodiment. According to the first embodiment, the ultrasonic diagnostic apparatus 1 specifically detects a saturated signal out of a saturated signal and an unsaturated signal by using an odd harmonic component included in a reflected wave signal. Subsequently, the ultrasonic diagnostic apparatus 1 selectively reduces the contribution of the saturated signal by multiplying the saturated signal by a weight coefficient. With this configuration, the ultrasonic diagnostic apparatus 1 can reduce the probability of reducing the contribution of an unsaturated signal by reducing the probability of erroneously determining an unsaturated signal to be a saturated signal. As a result, the ultrasonic diagnostic apparatus 1 can improve the visibility of an image because it forms an image from a reflected wave signal using an effective aperture in a broader range while reducing the influence of signal saturation. In particular, the above-described configuration exhibits more advantageous effects in imaging of a three-order harmonic component included in a reflected wave signal.

Second Embodiment

Figure 3:
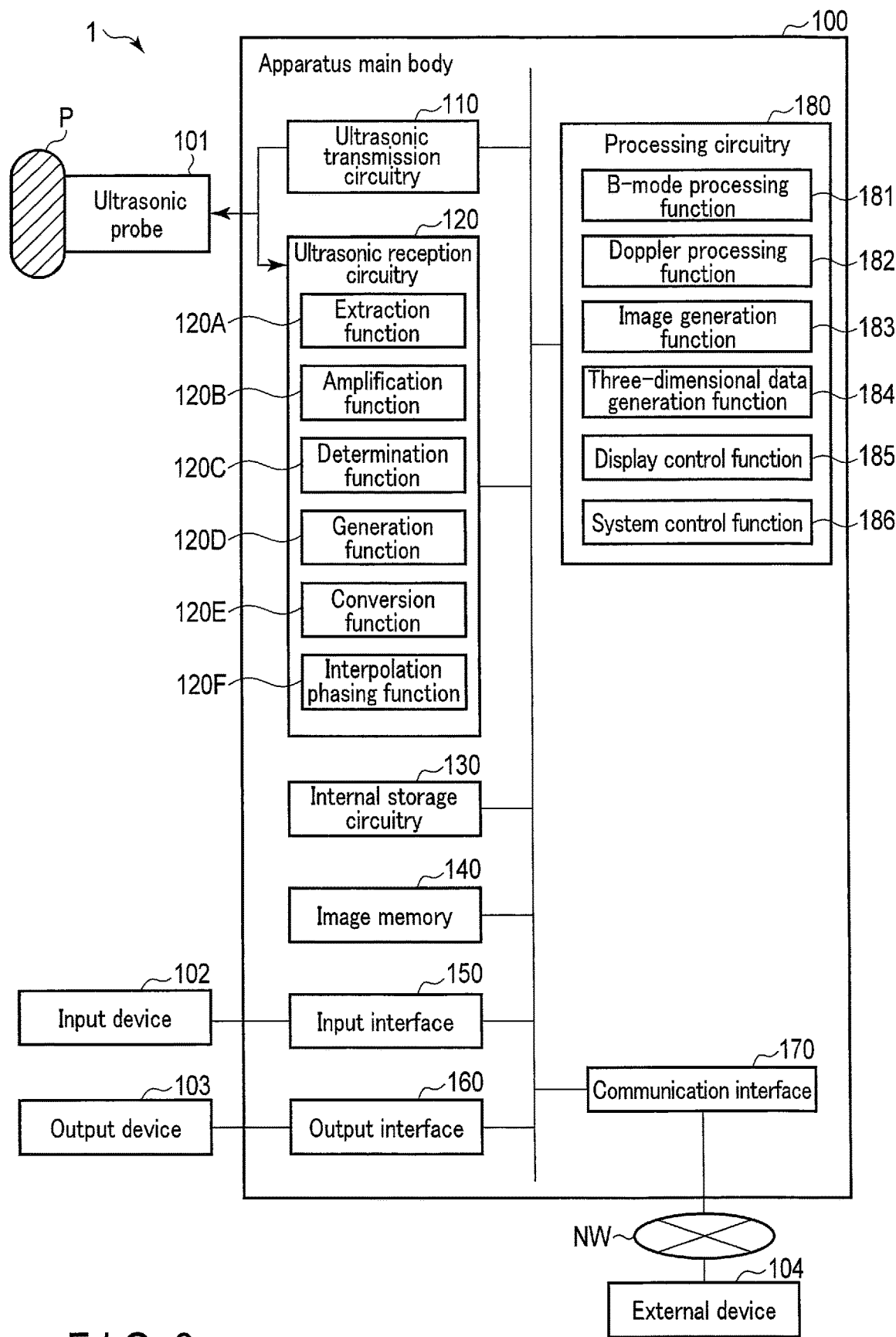
FIG. 3 is a diagram showing an example of a configuration of an ultrasonic diagnostic apparatus according to a second embodiment.

FIG. 3 is a diagram showing an example of a configuration of an ultrasonic diagnostic apparatus 1 according to a second embodiment. The configuration of the ultrasonic diagnostic apparatus 1 according to the second embodiment is generally the same as the configuration of the ultrasonic diagnostic apparatus 1 according to the first embodiment. The ultrasonic diagnostic apparatus 1 according to the second embodiment further includes a conversion function 120E and an interpolation phasing function 120F as the functions of the ultrasonic reception circuitry 120.

The conversion function 120E converts a reflected wave signal received by each element of the ultrasonic probe 101 to a baseband signal. The conversion function 120E may be implemented by quadrature detection circuitry.

The interpolation phasing function 120F performs interpolation and phasing on the baseband signal obtained by the conversion. The interpolation phasing function 120F may be implemented by the generator circuitry of the ultrasonic reception circuitry 120.

Figure 4:
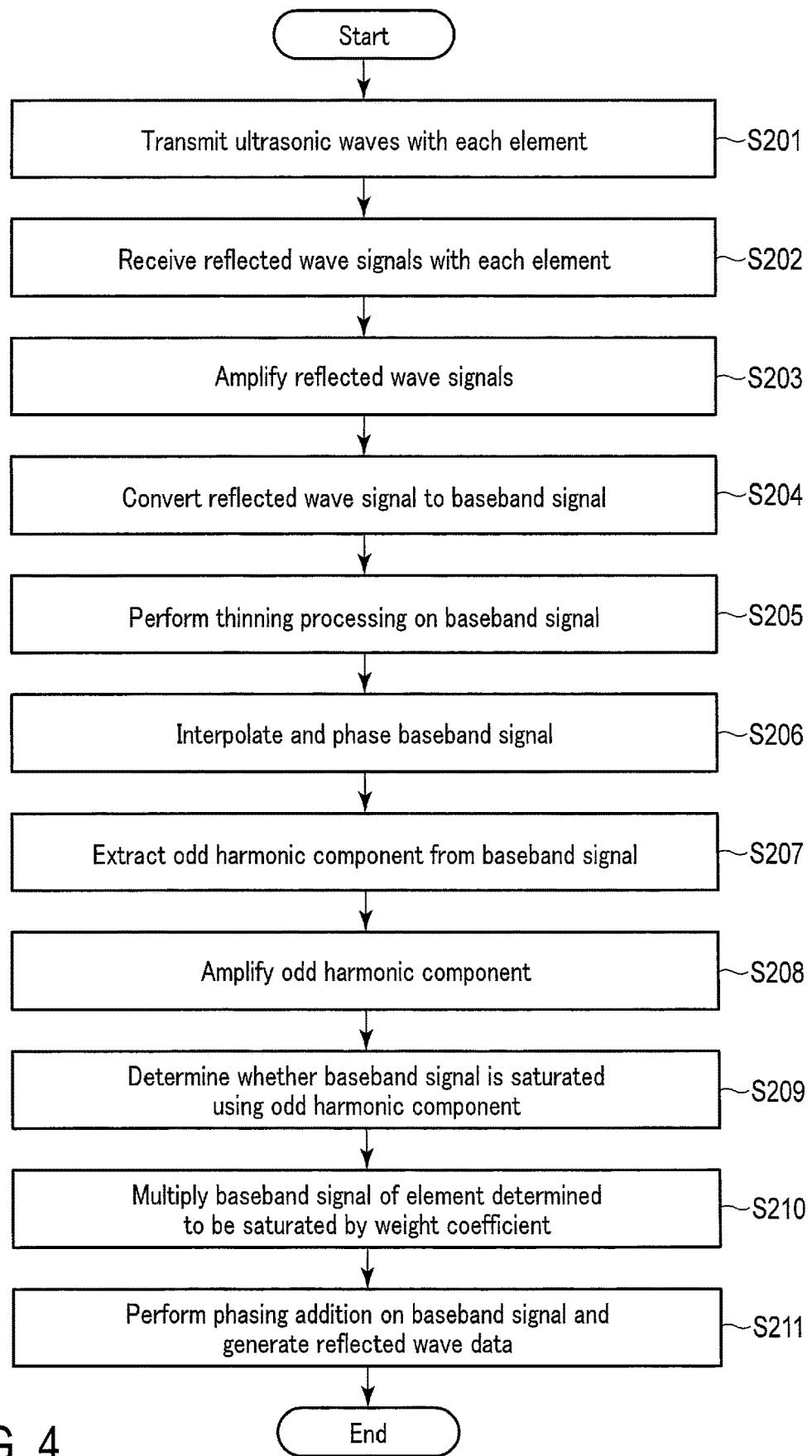
FIG. 4 is a diagram showing an example of an operation of the ultrasonic diagnostic apparatus according to the second embodiment.

FIG. 4 is a diagram showing an example of an operation of the ultrasonic diagnostic apparatus 1 according to the second embodiment. Unlike the first embodiment, the ultrasonic diagnostic apparatus 1 of the second embodiment converts a reflected wave signal to a baseband signal. That is, processing of generating reflected wave data based on the baseband signal is described. Since steps S201 to S203 are the same as steps S101 to S103, the descriptions thereof will be omitted.

In step S204, by implementing the conversion function 120E, the ultrasonic diagnostic apparatus 1 converts the reflected wave signal to a baseband signal.

In step S205, the ultrasonic diagnostic apparatus 1 performs thinning processing on the baseband signal.

In step S206, by implementing the interpolation phasing function 120F, the ultrasonic diagnostic apparatus 1 interpolates and phases the baseband signal.

In step S207, by implementing the extraction function 120A, the ultrasonic diagnostic apparatus 1 extracts an odd harmonic component from the baseband signal. Step S207 is similar to step S104.

In step S208, by implementing the amplification function 120B, the ultrasonic diagnostic apparatus 1 amplifies the extracted odd harmonic component. Step S208 is similar to step S105.

In step S209, by implementing the determination function 120C, the ultrasonic diagnostic apparatus 1 determines whether the baseband signal is saturated using the odd harmonic component. Step S209 is similar to step S106.

In step S210, by implementing the generation function 120D, the ultrasonic diagnostic apparatus 1 multiplies the baseband signal of the element determined to be saturated by a weight coefficient. Step S210 is similar to step S107.

In step S211, by implementing the generation function 120D, the ultrasonic diagnostic apparatus 1 performs phasing addition on the baseband signal and generates reflected wave data. Step S211 is similar to step S108.

The above is the description of the example of the operation of the ultrasonic diagnostic apparatus 1 according to the second embodiment. The result of the determination on the saturation of the baseband signal made by the ultrasonic diagnostic apparatus 1 based on the example of the operation and the result of the determination on the saturation of the baseband signal by an ultrasonic diagnostic apparatus according to a conventional configuration as a comparison will be described below.

Figure 5:
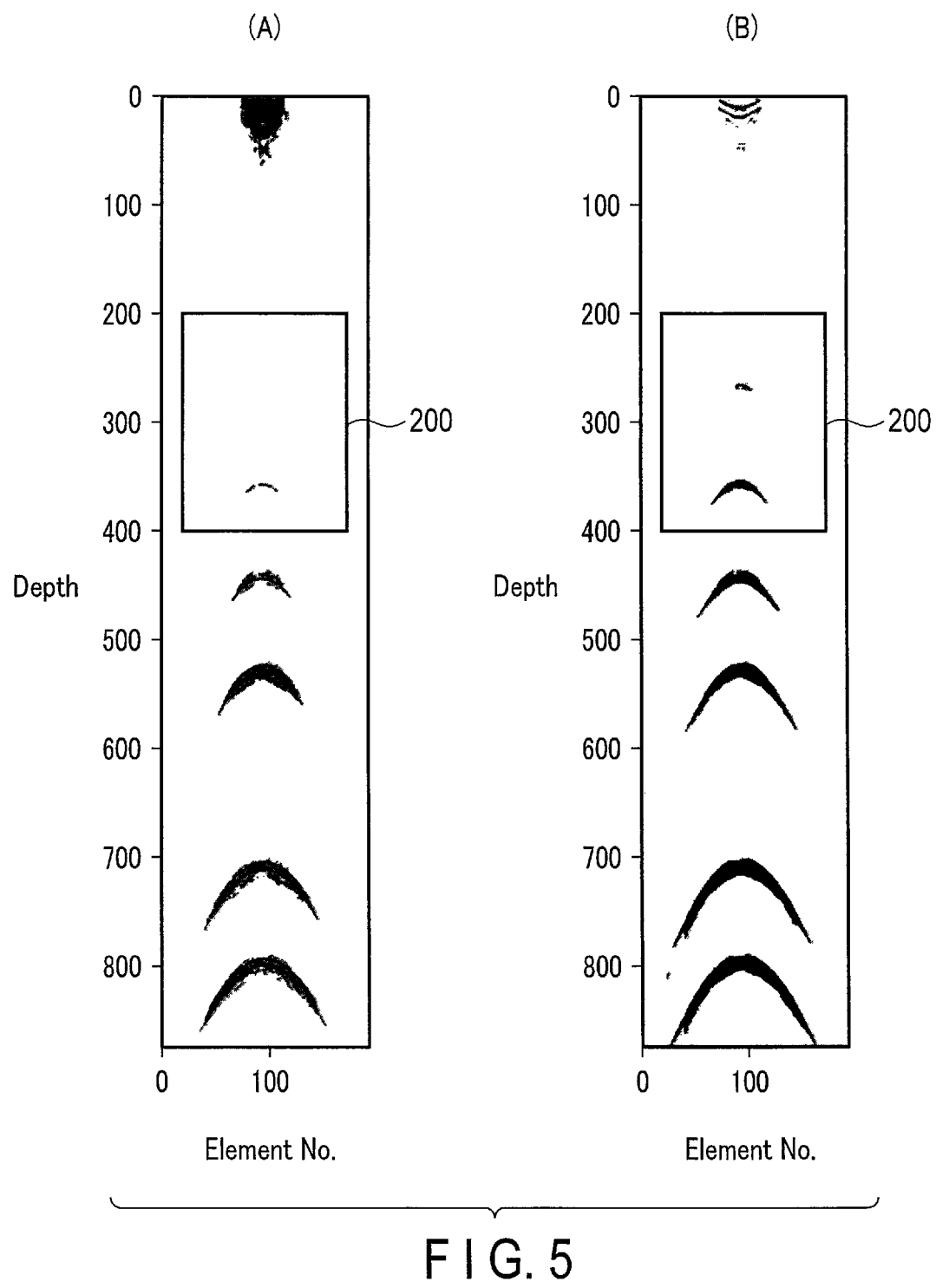
FIG. 5 is a diagram showing a result of determination on saturation of a baseband signal of each element of each ultrasonic diagnostic apparatus according to the second embodiment and a conventional configuration.

FIG. 5 is a diagram showing the result of the determination on the saturation of the baseband signal of each element of each of the ultrasonic diagnostic apparatuses according to the second embodiment and a conventional configuration.

The ultrasonic diagnostic apparatus 1 according to the second embodiment extracted an odd harmonic component from a baseband signal and determined whether the signal was saturated based on the amplitude of the extracted odd harmonic component. On the other hand, the ultrasonic diagnostic apparatus according to the conventional configuration determined whether the signal was saturated based on the amplitude of the baseband signal. Prior to the determination of saturation, each of the ultrasonic diagnostic apparatuses transmitted and received ultrasonic waves in the same experimental system.

In the aforementioned experimental system, six wires were arranged in a direction perpendicular to an ultrasonic transmission direction (depth direction) from a single element being a central element among the elements arranged in the ultrasonic probe of each ultrasonic diagnostic apparatus. Each wire was arranged generally at regular intervals in the depth direction from the central element in a tank filled with water. However, the interval between the fourth wire and the fifth wire in the order from the one closer to the central element in the depth direction was approximately twice as long as the interval between the other wires. In this experimental system, each of the ultrasonic diagnostic apparatuses transmitted ultrasonic waves with the ultrasonic probe being in contact with the water surface of the water tank, thereafter received reflected waves from each wire with each element, and obtained reflected wave signals. Each of the ultrasonic diagnostic apparatuses converted the reflected wave signals into baseband signals and thereafter determined whether the baseband signals for each depth in each element were saturated. The conditions for transmitting and receiving ultrasonic waves were set so that the reflected wave signals related to two wires from the shallower side among the six wires would be unsaturated signals and the reflected wave signals related to the remaining four wires would be saturated signals.

FIG. 5(A) shows the result of the determination on saturation made by the ultrasonic diagnostic apparatus 1 according to the second embodiment. FIG. 5 (B) shows the result of the determination on saturation made by the ultrasonic diagnostic apparatus according to the conventional configuration. In each of the figures, the horizontal axis represents the "element number" of each element of the ultrasonic probe, and the vertical axis represents the "depth" from each element. Approximately 200 elements are arranged in the array direction of the ultrasonic probe, and the central element corresponds to approximately the 100th element. The depth "0" generally corresponds to the depth at which the surface having each element of the ultrasonic probe arrayed thereon (acoustic radiation surface) is positioned. Herein, the baseband signals of each element determined to be saturated are indicated in black for each depth.

As is understood from each of the figures, saturation of the baseband signals is distributed in six arc shapes curved in the depth direction with the central element in the center. The arc-shaped distributions mean that the reflected waves generated at each wire reached the central element the fastest, whereas the farther the elements are located from the central element, the later the reflected waves reached the elements. Each of the arc-shaped distributions indicates saturation of the baseband signals generated from the reflected waves from each wire. Herein, determination of saturation is performed in the element signals before phasing processing is performed; however, determination of saturation may be performed after the interpolation phasing processing shown in step S206 is performed.

Herein, two distributions surrounded by the region 200 indicating the depth range of "200 to 400" are compared between FIG. 5(A) and FIG. 5(B). The two distributions indicate saturation of the baseband signals generated from each reflected wave from the first and the second wires in the order from the one closer to the central element in the depth direction. Specifically, in FIG. 5(A), the first distribution is not acknowledged, whereas the second distribution is slightly acknowledged. On the other hand, in FIG. 5(B), the first distribution is slightly acknowledged and the second distribution is fully acknowledged. That is, it is understood that the ultrasonic diagnostic apparatus 1 according to the second embodiment reduces the frequency of erroneously detecting unsaturated signals as saturated signals, as compared to the ultrasonic diagnostic apparatus 1 according to the conventional configuration.

Figure 6:
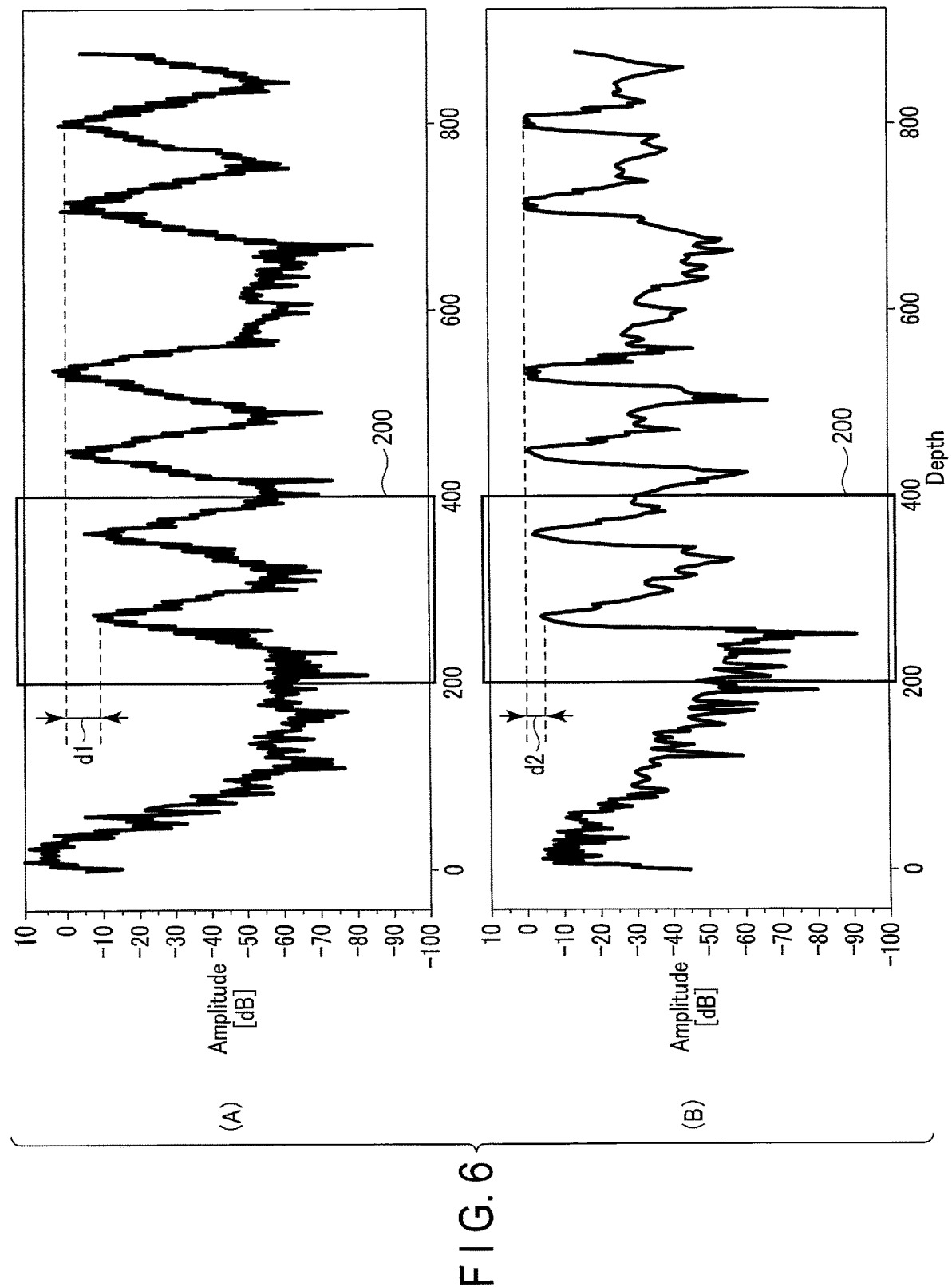
FIG. 6 is a diagram showing an amplitude of a baseband signal of a central element of each ultrasonic diagnostic apparatus according to the second embodiment and the conventional configuration.

FIG. 6 is a diagram showing the amplitude of the baseband signal of the central element of each of the ultrasonic diagnostic apparatuses according to the second embodiment and the conventional configuration. Specifically, each of FIGS. 6(A) and 6(B) shows the amplitude of the baseband signal for each depth of each of the central elements shown in FIGS. 5(A) and 5(B). In each of the figures, the horizontal axis represents the "depth" from each element of the ultrasonic probe (i.e., corresponding to the vertical axis of FIGS. 5(A) and 5(B)), and the vertical axis represents the amplitude in decibels. The region 200 shown in FIG. 5 corresponds to the region 200 shown in FIG. 6.

As is understood from each of the figures, six curved waveforms are recognized after the depth "200". Each of the waveforms indicates the amplitude of the baseband signal generated from the reflected wave from each wire. Herein, attention is paid to an amplitude difference between a value of an amplitude at the peak of the waveform in the shallowest position in the depth direction (the most left side) and a value of an amplitude at the peak of the waveform in the deepest position in the depth direction (the most right side). The amplitude difference is represented by "d1" in FIG. 6(A), and is represented by "d2" in FIG. 6(B). That is, the result of the processing performed by the ultrasonic diagnostic apparatus 1 according to the second embodiment corresponds to "d1", and the result of the processing performed by the ultrasonic diagnostic apparatus according to the conventional configuration corresponds to "d2". Specifically, d1 indicates the range of about "0 to −10 dB", and d2 indicates the range of about "0 to −5 dB". That is, it is understood that d1 is increased by about 5 dB, as compared to d2.

The ultrasonic diagnostic apparatus 1 according to the second embodiment can discriminate between a saturated signal and an unsaturated signal with high precision, as shown in FIG. 5(A), by, for example, setting a threshold to "about −5 dB", which is a middle value of the amplitude difference of d1. On the other hand, the ultrasonic diagnostic apparatus according to the conventional configuration has difficulty in discriminating between a saturated signal and an unsaturated signal with high precision, as shown in FIG. 5(B), even if a threshold is set to a middle value of the amplitude difference of d2 since the amplitude difference of d2 is narrower than the amplitude difference of d1.

The above is the description of the ultrasonic diagnostic apparatus 1 according to the second embodiment. According to the second embodiment, even if reflected wave signals are converted to baseband signals, the same effects as those achieved by the first embodiment can be achieved.

According to at least one embodiment described above, the precision of discriminating a saturated signal can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
processing circuitry configured to:
extract a third-or higher-order odd harmonic component from a reflected wave signal received by each element of an ultrasonic probe;
determine whether the reflected wave signal is saturated or not using the extracted third-or higher-order odd harmonic component;
multiply the reflected wave signal of an element for which the reflected wave signal is determined to be saturated by a weight coefficient to decrease a contribution of the reflected wave signal of the element; and
generate reflected wave data by performing phasing addition on the reflected wave signal multiplied by the weight coefficient.

2. The ultrasonic diagnostic apparatus according to claim 1, wherein the processing circuitry is further configured to determine that the reflected wave signal is saturated if an amplitude of the extracted third-or higher-order odd harmonic component is equal to or greater than a threshold.

3. The ultrasonic diagnostic apparatus according to claim 1, wherein the processing circuitry is further configured to amplify an amplitude of the extracted third-or higher-order odd harmonic component with a gain value and determine that the reflected wave signal is saturated if the amplified amplitude of the third-or higher-order odd harmonic component is equal to or greater than a threshold.

4. The ultrasonic diagnostic apparatus according to claim 3, wherein the processing circuitry is further configured to determine the gain value according to the amplitude of the extracted third-or higher-order odd harmonic component and amplify the amplitude with the determined gain value.

5. The ultrasonic diagnostic apparatus according to claim 1, wherein the processing circuitry is further configured to extract the third-or higher-order odd harmonic component from the reflected wave signal by applying frequency filtering processing for passing through a third-or higher-order odd harmonic band to the reflected wave signal received by each element of the ultrasonic probe.

6. The ultrasonic diagnostic apparatus according to claim 1, wherein the processing circuitry is further configured to:
cause the ultrasonic probe to perform ultrasound scanning with a set of a first transmission ultrasonic wave and a second transmission ultrasonic wave having a phase corresponding to an inverted phase of the first transmission ultrasonic wave;
add a reflected wave signal of the first transmission ultrasonic wave and a reflected wave signal of the second transmission ultrasonic wave that are received by each element of the ultrasonic probe; and extract the third-or higher order odd harmonic component from the added reflected wave signals by applying frequency filtering processing for passing through a third-or higher-order odd harmonic band to the added reflected wave signals.

7. The ultrasonic diagnostic apparatus according to claim 1, wherein the processing circuitry is further configured to cause the ultrasonic probe to perform ultrasound scanning with a set of a first transmission ultrasonic wave, a second transmission ultrasonic wave having a phase corresponding to a phase of the first transmission ultrasonic wave modulated at N degrees in a positive direction, and a third transmission ultrasonic wave having a phase corresponding to a phase of the first transmission ultrasonic wave modulated at N degrees in a negative direction, wherein N is a real number satisfying 0<N<180, and the processing circuitry is configured to:
add a reflected wave signal of the first transmission ultrasonic wave, a reflected wave signal of the second transmission ultrasonic wave, and a reflected wave signal of the third transmission ultrasonic wave that are received by each element of the ultrasonic probe; and extract the third-or higher-order odd harmonic component from the added reflected wave signals by applying frequency filtering processing for passing through a third-or higher-order odd harmonic band to the added reflected wave signals.

8. The ultrasonic diagnostic apparatus according to claim 1, wherein the processing circuitry is further configured to:
convert the reflected wave signal received by each element of the ultrasonic probe to a baseband signal;
perform interpolation and phasing on the baseband signal obtained by the conversion;
extract a third-or higher-order odd harmonic component from the interpolated and phased baseband signal;
determine whether the interpolated and phased baseband signal is saturated or not using the extracted third-or higher-order odd harmonic component;
multiply the interpolated and phased baseband signal of an element for which the interpolated and phased baseband signal is determined to be saturated by a weight coefficient to decrease a contribution of the interpolated and phased baseband signal of the element; and
generate the reflected wave data by performing phasing addition on the interpolated and phased baseband signal multiplied by the weight coefficient.

9. An ultrasonic diagnostic method comprising:
extracting a third-or higher-order odd harmonic component from a reflected wave signal received by each element of an ultrasonic probe;
determining whether the reflected wave signal is saturated or not using the extracted third-or higher-order odd harmonic component;
multiplying the reflected wave signal of an element for which the reflected wave signal is determined to be saturated by a weight coefficient to decrease a contribution of the reflected wave signal of the element; and
generating reflected wave data by performing phasing addition on the reflected wave signal multiplied by the weight coefficient.

10. The ultrasonic diagnostic apparatus according to claim 1, wherein the processing circuitry is further configured to increase an amplitude difference between an amplitude of a third-or higher-order odd harmonic component of a saturated reflected wave signal and an amplitude of a harmonic component of an unsaturated reflected wave signal by amplifying an amplitude of the extracted third-or higher-order odd harmonic component with a gain value.

11. The ultrasonic diagnostic apparatus according to claim 10, wherein the processing circuitry is further configured to set a threshold for a middle value of the amplitude difference.

* * * * *